United States Patent
Smith et al.

(10) Patent No.: US 11,890,006 B2
(45) Date of Patent: Feb. 6, 2024

(54) SYSTEMS, DEVICES, AND RELATED METHODS FOR FASTENING TISSUE

(71) Applicant: Boston Scientific Scimed, Inc., Maple Grove, MN (US)

(72) Inventors: Paul Smith, Smithfield, RI (US); Ryan V. Wales, Northborough, MA (US); Michael Peachock, Cleveland, OH (US); Nathan Cummings, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 160 days.

(21) Appl. No.: 16/936,760

(22) Filed: Jul. 23, 2020

(65) Prior Publication Data

US 2021/0022733 A1 Jan. 28, 2021

Related U.S. Application Data

(60) Provisional application No. 62/878,141, filed on Jul. 24, 2019.

(51) Int. Cl.
| | | |
|---|---|---|
| *A61B 17/068* | (2006.01) | |
| *A61B 17/00* | (2006.01) | |
| *A61B 17/072* | (2006.01) | |

(52) U.S. Cl.
CPC .... *A61B 17/0686* (2013.01); *A61B 17/00234* (2013.01); *A61B 17/072* (2013.01); *A61B 2017/00477* (2013.01); *A61B 2017/07257* (2013.01); *A61B 2017/07271* (2013.01); *A61B 2017/07285* (2013.01)

(58) Field of Classification Search
CPC .......... A61B 17/0686; A61B 17/00234; A61B 17/072; A61B 17/07207; A61B 2017/00477; A61B 2017/07257; A61B 2017/07271; A61B 2017/07285;
(Continued)

(56) References Cited

U.S. PATENT DOCUMENTS 4,848,637 A * 7/1989 Pruitt .................... A61B 17/072
227/19
5,074,454 A * 12/1991 Peters .............. A61B 17/07207
227/19
(Continued)

FOREIGN PATENT DOCUMENTS

WO 2020180678 A1 9/2020

*Primary Examiner* — Robert F Long
*Assistant Examiner* — Eduardo R Ferrero
(74) *Attorney, Agent, or Firm* — Bookoff McAndrews, PLLC

(57) ABSTRACT

According to one aspect, a fastening device may include a coupling body having (1) a portion configured to couple to a distal end of a medical device, (2) a cartridge holder, and (3) an anvil pivotably coupled to the cartridge holder. The cartridge holder and the anvil may extend distally from the portion and may be configured to extend distally of a distalmost face of the medical device when the portion is coupled to the distal end of the medical device. A flexible member may be configured to extend through a channel of the medical device. A fastener cartridge may be coupled to a distal end of the flexible member, including at least one fastener, and may be configured for releasable coupling to the cartridge holder.

20 Claims, 4 Drawing Sheets

(58) Field of Classification Search
CPC .... A61B 2017/00296; A61B 2017/003; A61B 2017/0034; A61B 2017/00858
See application file for complete search history.

(56) References Cited

U.S. PATENT DOCUMENTS

| | | | | |
|---|---|---|---|---|
| 5,389,098 | A * | 2/1995 | Tsuruta | A61B 17/07207 606/49 |
| 5,624,452 | A * | 4/1997 | Yates | A61B 18/1447 606/139 |
| 5,632,432 | A * | 5/1997 | Schulze | A61B 17/07207 227/176.1 |
| 5,692,668 | A * | 12/1997 | Schulze | A61B 17/07207 227/176.1 |
| 5,709,334 | A * | 1/1998 | Sorrentino | A61B 17/07207 227/176.1 |
| 6,032,849 | A * | 3/2000 | Mastri | A61B 17/07207 227/176.1 |
| 6,079,606 | A * | 6/2000 | Milliman | A61B 17/068 227/176.1 |
| 6,109,500 | A | 8/2000 | Alli et al. | |
| 6,119,913 | A * | 9/2000 | Adams | A61B 17/115 227/176.1 |
| 6,264,086 | B1 * | 7/2001 | McGuckin, Jr. | A61B 17/07207 606/167 |
| 8,439,246 | B1 * | 5/2013 | Knodel | A61B 17/068 227/176.1 |
| 8,701,960 | B1 * | 4/2014 | Manoux | A61B 17/07207 227/19 |
| 8,747,421 | B2 * | 6/2014 | Balbierz | A61B 17/072 227/176.1 |
| 9,808,248 | B2 * | 11/2017 | Hoffman | A61B 17/07207 |
| 10,335,147 | B2 * | 7/2019 | Rector | A61B 17/068 |
| 2006/0011699 | A1 * | 1/2006 | Olson | A61B 17/07207 227/19 |
| 2006/0025809 | A1 * | 2/2006 | Shelton, IV | A61B 17/07207 606/205 |
| 2008/0169333 | A1 * | 7/2008 | Shelton | A61B 17/32 227/180.1 |
| 2010/0072253 | A1 * | 3/2010 | Baxter, III | A61B 17/07207 227/176.1 |
| 2011/0278343 | A1 * | 11/2011 | Knodel | A61B 17/07207 227/176.1 |
| 2012/0241499 | A1 * | 9/2012 | Baxter, III | A61B 17/105 227/176.1 |
| 2013/0299549 | A1 * | 11/2013 | Crews | A61B 17/068 227/175.1 |
| 2013/0306704 | A1 * | 11/2013 | Balbierz | A61B 17/29 227/176.1 |
| 2013/0334278 | A1 * | 12/2013 | Kerr | A61B 17/07207 227/175.1 |
| 2014/0001231 | A1 * | 1/2014 | Shelton, IV | A61B 34/37 227/175.3 |
| 2014/0005679 | A1 * | 1/2014 | Shelton, IV | A61B 17/068 606/130 |
| 2014/0021240 | A1 | 1/2014 | Miyamoto | |
| 2014/0231489 | A1 * | 8/2014 | Balbierz | A61B 17/068 227/178.1 |
| 2014/0239044 | A1 * | 8/2014 | Hoffman | A61B 17/07207 227/176.1 |
| 2014/0291380 | A1 * | 10/2014 | Weaner | A61B 17/07207 227/176.1 |
| 2014/0291381 | A1 * | 10/2014 | Weaner | A61B 17/07207 227/176.1 |
| 2014/0291382 | A1 * | 10/2014 | Lloyd | A61B 17/07207 227/176.1 |
| 2015/0001274 | A1 * | 1/2015 | Cole | A61B 17/072 227/176.1 |
| 2015/0238193 | A1 * | 8/2015 | Balbierz | A61B 17/115 227/176.1 |
| 2016/0058441 | A1 * | 3/2016 | Morgan | A61B 17/07207 606/219 |
| 2016/0270785 | A1 * | 9/2016 | Balbierz | A61B 17/0686 |
| 2016/0278774 | A1 * | 9/2016 | Shelton, IV | A61B 17/105 |
| 2016/0361059 | A1 * | 12/2016 | Balbierz | A61F 5/0086 |
| 2019/0000535 | A1 * | 1/2019 | Messerly | A61B 18/1445 |
| 2019/0321035 | A1 * | 10/2019 | Balbierz | A61F 5/0086 |
| 2021/0369274 | A1 * | 12/2021 | Kostrzewski | A61B 17/07207 |

\* cited by examiner

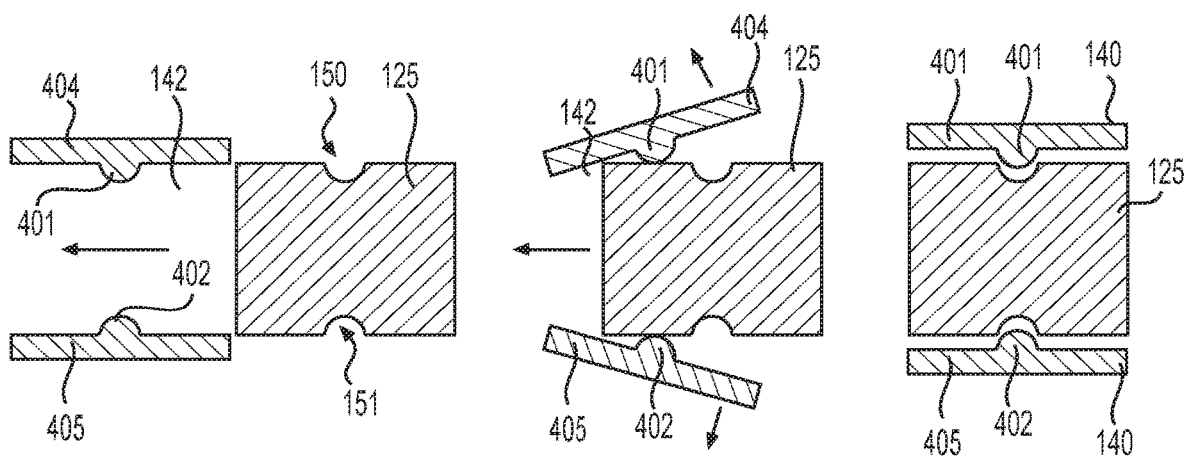
*FIG. 4A*  *FIG. 4B*  *FIG. 4C*
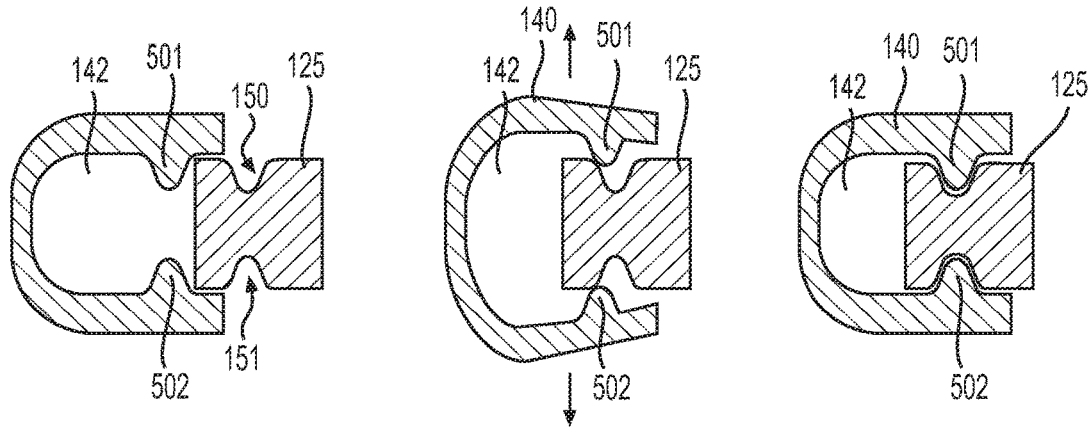
*FIG. 5A*  *FIG. 5B*  *FIG. 5C*
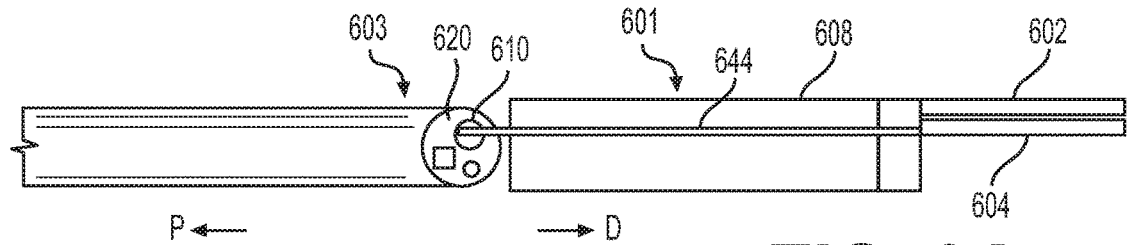
*FIG. 6A*
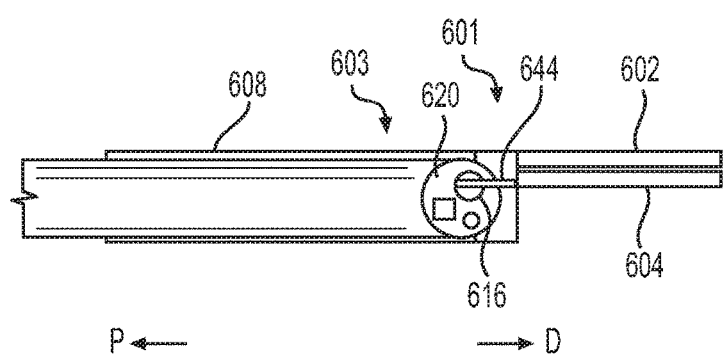
*FIG. 6B*

SYSTEMS, DEVICES, AND RELATED METHODS FOR FASTENING TISSUE

CROSS-REFERENCE TO RELATED APPLICATIONS

This application claims the benefit of priority from U.S. Provisional Application No. 62/878,141, filed Jul. 24, 2019, which is incorporated by reference herein in its entirety.

TECHNICAL FIELD

The present disclosure relates generally to tissue closure. More particularly, at least some embodiments of the present disclosure relate to a stapling mechanism for a medical device, for example an endoscopic stapler, and related methods of using the stapling mechanism.

BACKGROUND

Stapling is used in many medical procedures, including laparoscopic procedures for example. These procedures often involve resecting portions or sections of tissue, followed by closing using staples. An exemplary procedure is colorectal anastomosis. In hybrid surgeries where physicians use laparoscopic and endoscopic platforms to conduct a procedure, a rigid stapler is often used. Linear staplers, which may include long rigid members, may be incapable of being navigated through tortuous anatomy without causing trauma to the tissue.

SUMMARY

Aspects of the disclosure relate to, among other things, systems, devices, and methods for fastening tissue. Each of the aspects disclosed herein may include one or more of the features described in connection with any of the other disclosed aspects.

According to one aspect, a fastening device may include a coupling body having (1) a portion configured to couple to a distal end of a medical device, (2) a cartridge holder, and (3) an anvil pivotably coupled to the cartridge holder. The cartridge holder and the anvil may extend distally from the portion and may be configured to extend distally of a distalmost face of the medical device when the portion is coupled to the distal end of the medical device. A flexible member may be configured to extend through a channel of the medical device. A fastener cartridge may be coupled to a distal end of the flexible member, including at least one fastener, and may be configured for releasable coupling to the cartridge holder.

In other aspects of the present disclosure, the device may include one or more of the features below. The fastener cartridge may include a protrusion, and the cartridge holder may include a recess configured to receive the protrusion. The recess may be a first recess and the protrusion may be a first protrusion, and the fastener cartridge may include a second protrusion, and the cartridge holder may include a second recess configured to receive the second protrusion. The device may include a knife for cutting tissue. The knife may be configured to move from a cavity within the cartridge holder through a channel of the fastener cartridge. A distalmost end of the fastener cartridge may be distal to the cavity when the fastener cartridge is coupled to the cartridge holder. The knife may be configured to move proximally from a cavity at a distal portion of the cartridge holder. The knife may be positioned adjacent to the fastener cartridge and within a channel of the cartridge holder as the knife moves proximally. The knife may include a first proximally-facing sharp edge. The anvil may include a channel configured to receive the knife. The cartridge holder may include a channel for receiving the fastener cartridge; and at least one tang may extend into the channel. The fastener cartridge may include at least one recess configured to receive at least one tang, and the at least one tang may be positioned within the at least one recess when the fastener cartridge is coupled to the cartridge holder. The anvil may include a distal portion and two spaced-apart proximal portions extending from the proximal end of the distal portion, and each of the two proximal portions may be pivotably coupled to the coupling body. The flexible member may be a first flexible member, and the device further include a second flexible member coupled to the coupling body and configured to extend to a proximal portion of the medical device, and an actuation wire extending through the second flexible member. The actuation wire may be configured to move the anvil towards and/or away from the cartridge holder. The cartridge holder may include a protrusion at a distal portion of the cartridge holder, and the protrusion may be configured to contact the anvil, when the anvil is moved towards the cartridge holder, to stop movement of the anvil towards the cartridge holder and leave a space between the fastener cartridge and the anvil. The coupling body may include a flange configured to limit the movement of the anvil relative to the cartridge holder. The flexible member may include at least one actuation wire configured to deploy the at least one fastener from the fastener cartridge.

In other aspects, a medical device may include a flexible member configured to extend through a channel of an endoscope; and a stapler cartridge may be coupled to a distal end of the flexible member and may include a plurality of staples. The stapler cartridge may be configured to extend through the channel of an endoscope and may be removably couple to a cartridge holder.

In other aspects of the present disclosure, the device may include one or more of the features below. The stapler cartridge may include a protrusion configured to be positioned within a recess of the cartridge holder when the fastener cartridge is coupled to the cartridge holder. The stapler cartridge may define a longitudinal channel configured to receive a knife.

In other aspects, a medical method may include inserting a flexible medical device including into a natural orifice of a body; deploying at least one fastener from a fastener cartridge coupled to a cartridge holder at a distal end of the medical device; uncoupling the fastener cartridge from the cartridge holder, while the flexible medical device, the cartridge holder, and the fastener cartridge are in the body; and removing the fastener cartridge from the body by moving the fastener cartridge proximally through a channel of the medical device.

In other aspects, the medical method other aspects of the present disclosure, the method may include one or more of the features below. The fastener cartridge may be a first fastener cartridge, and the method may further include moving a second fastener cartridge distally through the channel, while the flexible medical device is in the body; and coupling the second fastener cartridge to the cartridge holder.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 4A-4C are cross-sectional views of a portion of an exemplary coupling feature for a medical device, according to aspects of this disclosure.

FIGS. 5A-5C are cross-sectional views of a portion of an exemplary coupling feature for a medical device, according to aspects of this disclosure.

FIGS. 6A and 6B are side views of an exemplary medical device, according to aspects of this disclosure.

DETAILED DESCRIPTION

The present disclosure is drawn to systems, devices, and methods for coupling, cutting, dissection, and/or resection of tissue, among other aspects. Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. Throughout the figures, the distal direction is shown as an arrow labeled "D", and the proximal direction is shown as an arrow labeled "P". The term "coupling tissue together" may refer, for example, to stapling, fixing, attaching, fastening, or otherwise joining two portions of tissue together. The term "fastener" may include staples, clips, elastic bands, suture, or any other fastener known in the art. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

Embodiments of the present disclosure may be used to visualize, resect, and/or couple together target tissue in an endo-luminal space, or facilitate the process thereof. In particular, some embodiments combine a tissue resecting device with a tissue stapling device. Other embodiments may include a stapling device without a resection mechanism. For example, the apparatus may include a resection, or cutting, mechanism (e.g., an integrated knife) and a stapling mechanism (stapler). The apparatus may be coupled to an endoscope, arthroscope, colonoscope, uteroscope, sheath, catheter, or other medical device and delivered to a target tissue site via that device. In some examples, a cartridge for holding fasteners, such as staples, may be delivered to the apparatus via a working channel of the medical device in which the apparatus is coupled. All or parts of the apparatus could be metallic, plastic, or include a shape memory metal (such as nitinol), a shape memory polymer, a polymer, or any combination of materials.

Figure 1:
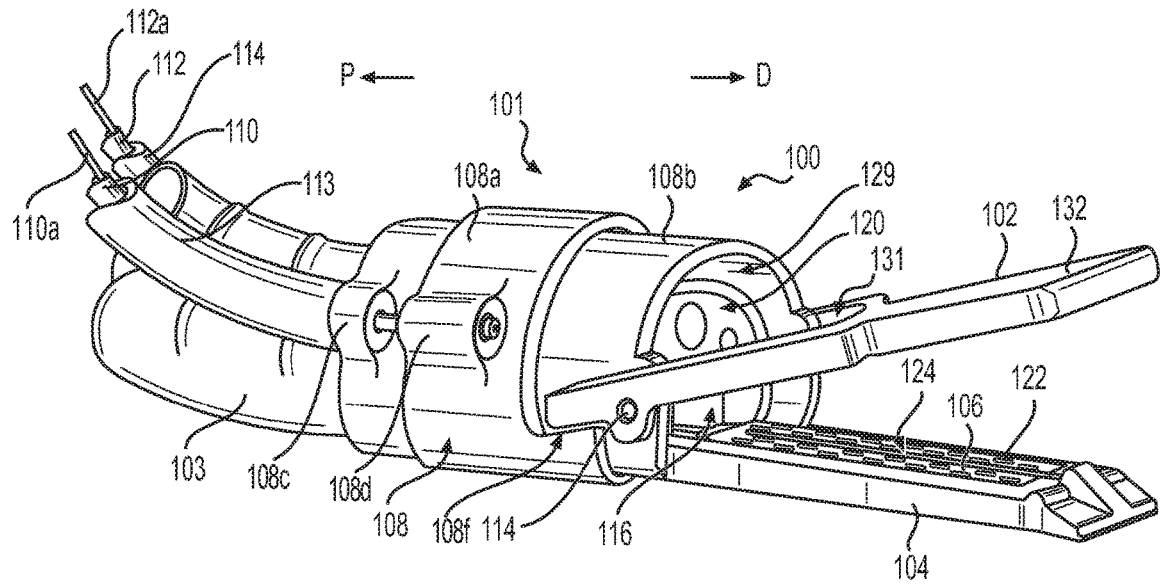
FIG. 1 is a perspective view of an exemplary medical device coupled to an endoscope, according to aspects of this disclosure.

FIG. 1 shows a distal portion of a medical apparatus 101 coupled to a distal tip 100 of an endoscope 103, in accordance with an embodiment of this disclosure. Apparatus 101 may be a surgical stapling apparatus configured to engage body tissue, apply one or more fasteners thereto, and, optionally, form an incision in the fastened body tissue during minimally invasive procedures, such as laparoscopic or endoscopic procedures. Apparatus 101 may be removably coupled to a distal tip 100 of a medical device, such as endoscope 103. Tip 100 is covered by a portion of apparatus 101 in FIG. 1. Apparatus 101 may be used to apply surgical clips or other fasteners, but will be primarily discussed in the context of applying staples from a staple cartridge positioned in a portion of the device's body, such as a loading unit.

As illustrated in FIG. 1, a distal section of apparatus 101 may include a coupling body or first body 108, a second body 104 coupled to the first body 108, an anvil 102, a cartridge 106, and two elongate bodies 110, 112 extending from the distal section of apparatus 101 to a proximal section. Each elongate body 110, 112 may extend any length suitable for endoscopic or laparoscopic procedures, and may, in some examples, be configured to be positioned adjacent to a radially-outer surface of endoscope 103 or other medical device. Elongate bodies 110, 112 may be coupled to an actuation assembly, such as a handle with one or more actuators, at the proximal ends of each elongate body 110, 112. In some examples, each elongate body 110, 112 may be flexible and/or may be rotatable about its axis. Elongate bodies 110, 112 may be positioned within cover elongates 113, 114 and may extend through a longitudinal lumen of cover elongates 111, 113. Cover elongates 111, 113 may be a polymer material and may protect elongate bodies 110, 112 from contacting an interior surface of a patient's body. Each elongate body 110, 112 may include a lumen for positioning actuation wires within.

These actuation wires positioned within one or more lumens of one or more elongate bodies 110, 112 can serve a variety of possible functions. In one exemplary embodiment, first body 108 may include interior channels (not shown) in which elongate bodies 110, 112 (or only wires 110a, 112a of bodies 110, 112) extend, so that distal ends of those bodies 110, 112 connect with anvil 102 (to pivot anvil 102 about pivot point 114) and/or with an actuation mechanism within second body 104 that deploys staples. Wires 110a, 112a may extend from anvil 102 through a lumen within first body 108 to provide a means to move anvil 102 between an open position (shown in FIG. 1) and a closed position in which a portion of anvil 102 contacts second body 104. In other examples, wires (such as 110a, 112a) may extend from anvil 102 outside of first body 108. In these examples, actuation wires (such as wires 110a, 112a) may be coupled to a position on anvil 102 such that movement of the actuation wires will cause anvil 102 to pivot about first pivot point 114 and a second pivot point (not shown) at an opposite side of first body 108 as the first pivot point 114. In some examples, a biasing member may bias anvil 102 towards an open position (shown in FIG. 1), and pulling one or more wires (such as wires 110a, 112a) coupled to anvil 102 near pivot points 114 may move anvil 102 from an open position to a closed position. In some examples, elongate bodies 110, 112 could each be a bowden cable comprised of a wire within a coil/sheath. In some examples, elongate bodies 110, 112 may be fixedly coupled to first body 108, and in other examples the elongate bodies 110, 112 may be removably or releasably coupled to first body 108. In some examples (not shown), apparatus 101 may include only one elongate body 110, 112 or more than two elongate bodies 110, 112.

Figure 2:
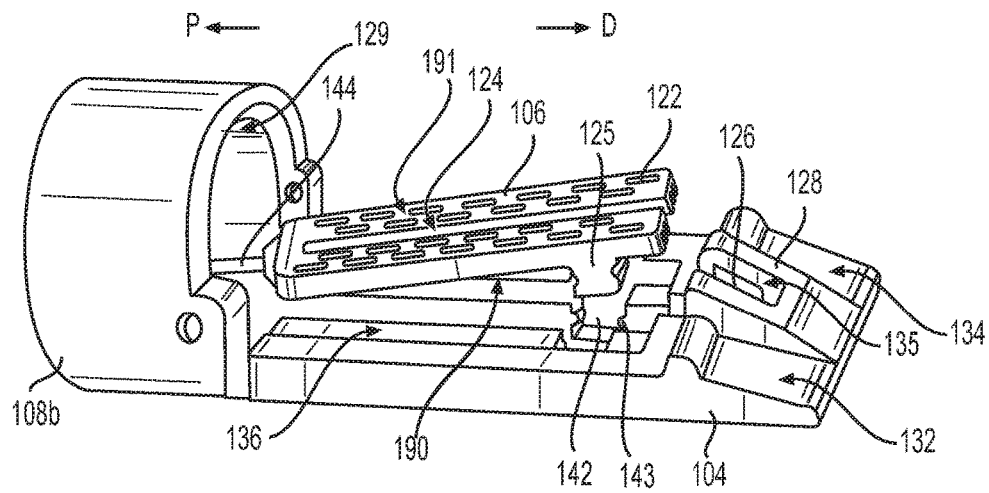
FIG. 2 is a perspective view of an exemplary portion of the medical device of FIG. 1, according to aspects of this disclosure.

First body 108 may be configured to support anvil 102 and second body 104. For example, a distal tip 100 of an endoscope 103 may be inserted into a lumen 129 of first body 108 to couple apparatus 101 to distal tip 100. In some examples, first body 108 may be annular and/or partially annular, and may be configured to receive a distal tip 100 of an endoscope 103 or other medical device. In some examples, first body 108 may include a first annular portion 108a that receives a second annular portion 108b, and second annular portion 108b may be configured to coupled to distal tip 100. First body 108 may include a first radial protrusion 108c positioned on a radially-outermost surface of second annular portion 108b, and may include a second radial protrusion 108d positioned on a radially-outermost surface of first annular portion 108a. In some examples, additional annular protrusions (not shown) may be positioned on first body 108. The first annular protrusion 108c and second annular protrusion 108d may include openings to internal channels of first body 108, and may be configured to receive elongate bodies 110, 112, cover elongates 111, 113, and/or wires 110a, 112a. A distal flange 108f of first annular portion 108a may be positioned proximate to pivot point 114 and may limit the rotation of anvil 102. FIG. 2 shows apparatus 101 with anvil 102, a portion of second annular portion 108b, and elongates 110, 112 removed. First body 108 may include a rough or irregular radially-inner surface within lumen 129 that may facilitate coupling first body 108 to endoscope 103, via a friction or interference fit.

In some examples, a distal front face 120 of distal tip 100 may contact a proximal surface of second body 104 when fully inserted within lumen 129 of first body 108, so that body 104 acts as a stop for insertion of endoscope 103.

Anvil 102 may be rotatably or pivotably coupled to a proximal portion of first body 108 at one or more pivot points 114. Anvil 102 may be Y-shaped (e.g., having two proximal arms each extending to an anvil distal portion 132) and may extend distally from first body 108. In some examples, anvil 102 may be rotatably biased and may be biased to an open configuration, i.e. biased away from body 104 and cartridge 106, creating a space between distal portion of anvil 102 and the distal portion of body 104 and cartridge 106. Anvil 102 may be rotatable to contact body 104, or pinch tissue between anvil 102 and body 104, and provide a surface for which staples may be driven when ejected from cartridge 106. A space 131 between a distal portion 132 of anvil 102 and distal front face 120 of endoscope 103 may provide space for one or more tools to be positioned distal to distal front face 120 of endoscope 103, when anvil 102 is in a closed or open position. For example, space 131 may allow a user to pull tissue between anvil 102 and second body 104, and then a user may actuate anvil 102 to sandwich the tissue between anvil 102 and second body 104, without the tool preventing anvil 102 from fulling closing onto second body 104.

Second body 104 may be fixedly coupled to first body 108 and may extend distally from first body 108. In other examples (not shown), second body 104 may be pivotally coupled to first body 108 and may rotate relative to a fixed anvil. Second body 104 may be longitudinally aligned with endoscope 103 when apparatus 101 is coupled to endoscope 103, such that a central longitudinal axis of endoscope 103 is substantially parallel to a longitudinal axis of second body 104. When apparatus 101 is coupled to distal tip 100, second body 104 may be configured to align with a working channel 116 of endoscope 103 and/or extend adjacent to a central longitudinal axis of working channel 116. Second body 104 may include one or more cavities at a distal portion of second body 104, and the one or more cavities may be configured to receive one or more actuators, such as an actuation sled or actuation mechanism for deploying staples. Cavities may be within distal portions 132, 134 and may be configured to hold one or more actuation sleds and/or one or more devices for cutting tissue (such as knives). For example, distal portion 128 (shown in FIG. 2 with a top surface of distal portion 128 removed) of second body 104 may be configured to receive a knife 126 for cutting tissue. In some examples, distal portion 128 may include a pocket 135 configured to receive knife 126 and prevent knife 126 from contacting a patient's tissue during insertion of apparatus into the patient or during certain other procedural steps, such as stapling. Distal portion 128 and pocket (or cavity) 135 may protrude from the top surface 191 of cartridge 106 such that anvil 102 contacts distal portion 128 when in a closed position, thus creating a gap between anvil 102 and top surface 191 of cartridge 106. By creating a gap between anvil 102 and top surface 191, this gap may provide adequate space for one or more tissue layers. In some examples, anvil 102 may include a recess (not shown) configured to receive distal portion 128 of second body 104, when anvil 102 is in a closed position.

In some examples, second body 104 may include a channel 136 that supports cartridge 106. The channel 136 may extend along the second body 104 in a direction substantially parallel with a central longitudinal axis of the endoscope 103. Cartridge 106 may contain a plurality of surgical fasteners, such as staples, and the fasteners may be deployed from cartridge 106 when under the influence of a driving force, such as a driving force supplied by an actuator moving through or along cartridge 106. A plurality of spaced apart longitudinal slots 122 in cartridge 106 allow staples to pass through cartridge 106 and pierce tissue. In some examples, an actuation sled or mechanism is movable proximally in the longitudinal direction from a distal end of cartridge 106 and/or second body 104 when actuated, contacting fasteners within cartridge 106 and pushing fasteners through longitudinal slots 122 in order to couple fasteners to tissue. In some examples, fasteners may be deployed from cartridge 106 in the same or similar manner as disclosed in U.S. Patent Application No. 62/812,538, titled "Systems, Devices, and Related Methods for Fastening Tissue," filed Mar. 1, 2019, the contents of which are incorporated herein by reference in their entirety. Fasteners may pierce tissue and contact anvil 102 to couple fasteners to tissue. In some examples, a single fastener may extend through each slot 122. Each fastener may be partially within a slot 122 prior to deployment to assist with alignment of the fastener with the slot 122. In some examples, different actuators may be required to actuate different longitudinal rows of fasteners in cartridge 106.

Cartridge 106 may also include a longitudinal slot or channel 124. The longitudinal slot 124 may be configured to receive and/or support a resecting tool, such as knife 126 or other device for cutting tissue. The longitudinal slot 124 may be positioned in the middle of cartridge 106 and may run longitudinally from a proximal portion to the distal end of cartridge 106. In some examples, an equal number of spaced apart longitudinal slots 122 may be positioned on each side of the longitudinal slot 124. Anvil 102 may include a groove (not shown) positioned longitudinally that may align with longitudinal slot 124 when anvil 102 is in the closed position (e.g., anvil 102 is rotated such that a distal portion of anvil 102 comes into contact with second body 104 and/or cartridge 106, or pinches tissue between anvil 102 and body 104) and such groove may be configured to receive a resecting tool, such as knife 126 or other sharp cutting tool, within the longitudinal slot 124. The cutting tool may be actuated via an actuation wire or other mechanism to move knife 126 proximally. Cartridge 106 may be fixedly coupled to second body 104 or may be removable from second body 104. In some examples, cartridge 106 may be integrally formed in second body 104. Actuation wires for actuation sleds that may deploy fasteners and/or actuation wires for moving a device for resecting tissue (such as knife 126) may extend through one or more of elongate bodies 110, 112 and/or a proximal elongate member 144 of cartridge 106.

Figure 3:
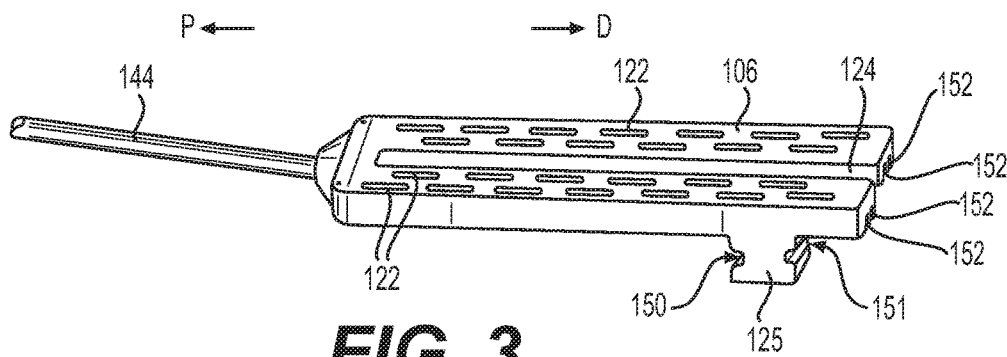
FIG. 3 is a perspective view of an exemplary portion of the medical device of FIG. 1, according to aspects of this disclosure.

FIG. 3 shows an exemplary cartridge 106 including slots 122, longitudinal slot 124, channels 152, proximal elongate member 144, and coupling protrusion 125. Channels 152 may extend longitudinally through cartridge 106 and may be configured to receive an actuator used to deploy fasteners from slots 122. In some examples, each channel 152 may house an actuator, such as an actuation sled, that may be configured to move from a distal end of cartridge 106 to a proximal end of cartridge 106, deploying fasteners as it moves proximally. For example, actuation sled may be an element such as a ramp or other component configured to engage and extend staples in an upward direction through the longitudinal slots 122 as the actuation sled is moved in a proximal direction. Proximal elongate member 144 may be fixedly coupled to cartridge 106 and may include one or more lumens. Proximal elongate member 144 may be configured to receive one or more actuation wires extending from cartridge 106 to a proximal portion of proximal elongate member 144. In some examples, proximal elongate member 144 may be flexible and may be configured to bend to allow movement through torturous pathways of a body of a patient. For example, proximal elongate member 144 may include one or more articulation joints (not shown) that allow proximal elongate member 144 to bend through torturous pathways. Suitable articulation joints may be any known in the art of medical devices, including endoscopic devices such as endoscopes, that permit pending of the device. In some examples, the proximal end of proximal elongate member 144 may include a spool-style handle or wheel-shaped knob that is configured to deploy the fasteners in cartridge 106 by either pulling or rotating the spool-style handle or wheel-shaped knob, for example, to actuate an actuation sled, though any suitable handle or actuator may be used. Cartridge 106 may be sized to fit within working channel 116 such that a user may move cartridge 106 through working channel 116 and couple cartridge 106 to second body 104. In some embodiments, the cartridge 106 may be replaceable to deploy additional staples without removing the endoscope and device 101 from a body lumen of a patient.

Coupling protrusion 125 may be positioned at a distal portion of cartridge 106 and may extend from a surface 190 on an opposite side of second body 104 from a surface 191 that includes slots 122. Coupling protrusion 125 may be configured to be positioned within a recess 142 of channel 136. In some examples, coupling protrusion 125 may be configured to removably couple cartridge 106 to second body 104. Coupling protrusion 125 may include recesses 150, 151 that may be configured to receive protrusions 143 in recess 142. Coupling protrusion 125 may extend from each side of cartridge 106 (e.g., substantially perpendicular to a central longitudinal axis of the endoscope 103) such that coupling protrusion 125 is on each side of channel 124, or coupling protrusion 125 may extend from only one side of channel 124. In some examples, coupling protrusion 125 and/or recess 142 may be one or more of a boss, protrusion, detent, fin, prong, hook, ball, divot, socket, recess, snap, tab, key, or restraint, or otherwise form a friction or interference fit. In some examples, coupling protrusion 125 may be overmolded. The surfaces defining recess 142 may be configured to deflect, bend and/or flex when coupling protrusion 125 is moved within recess 142 so as to provide a snap-fit between recess 142 and coupling protrusion 125.

FIGS. 4A-4C show cross-sectional views of an exemplary coupling mechanism that may be used to couple coupling protrusion 125 within recess 142. In FIG. 4A, coupling protrusion 125 of cartridge 106 is being inserted into recess 142. As shown in FIG. 4B, when coupling protrusion 125 contacts protrusions 401, 402 within recess 142, the side walls/surfaces 404, 405 forming recess 142 elastically deflect, or expand outward (shown via arrows in FIG. 4B) from the central longitudinal axis of recess 142, until recesses 150, 151 align with protrusions 401, 402. Once protrusions 401, 402 are positioned within recesses 150, 151, coupling protrusion 125 may be sufficiently coupled within recess 142 to withstand forces applied during medical procedures and remain within recess 142. FIGS. 5A-5C show cross-sectional views of an additional exemplary coupling mechanism that may be used to couple coupling protrusion 125 within recess 142 that is substantially similar to the coupling mechanism shown in FIGS. 4A-4C. In FIGS. 5A-5C, a portion of the material forming channel 142 expands outward as coupling protrusion 125 is inserted within recess 142. The material forming channel 142 may be biased such that protrusions 501, 502 move or snap into recesses 150, 151, to couple coupling protrusion 125 within recess 142. To position coupling protrusion 125 within recess 142, and thus couple cartridge 106 to second body 104 within channel 136, a user may pull, push, rotate, or otherwise move proximal elongate member 144, or use a separate tool inserted into an endoscope channel to couple cartridge 106 to second body 104. Similarly, a user may pull, push, rotate, or otherwise move proximal elongate member 144, or use a separate tool, to release cartridge 106 from second body 104. By providing a releasable couple mechanism between cartridge 106 and second body 104, a user may exchange cartridges using working channel 116 without removing apparatus 101 and endoscope 103 from a position within the body of a patient, which may prevent irritation or harm to the patient during a procedure and may reduce total procedure duration.

Prior to using apparatus 101 in a procedure, a user may couple apparatus 101 to an endoscope 103 and position proximal elongate member 144 with cartridge 106 within working channel 116. In some examples, a user may first couple first body 108 to distal tip 100 of endoscope 103, and then position proximal elongate member 144 in working channel 116 and couple cartridge 106 to channel 136 of second body 104. To use apparatus 101, cartridge 106 is positioned within channel 136 in order to deploy fasteners from cartridge 106. A user may use apparatus 101 to couple one or more fasteners to tissue by first positioning tissue within an active region of the apparatus 101 between anvil 102 and second body 104. Once tissue is positioned in the active region of apparatus 101, a user may actuate an actuator through one or more of elongate bodies 110, 112, as described above, which may then cause anvil 102 to close onto the tissue positioned within the active region. While the user holds anvil 102 in a closed position, thus maintaining the stapler device's clasp on the tissue, the user may deploy one or more staples from slots 122, for example by pulling proximally on an actuator to translate an actuation wire coupled to an actuation sled in the cartridge 106 or second body 104. When an actuation sled or mechanism is translated proximally via the actuation wire, the actuator may push a fastener through a longitudinal slot 122 to pierce the tissue. When the fastener is deployed by the actuator, the fastener may subsequently engage anvil 102 and couple layers of tissue together. In some examples, the actuator may actuate an actuation wire coupled to both an actuation sled or mechanism and a resection tool (such as knife 126), and may translate both the actuation sled and the resection tool simultaneously to both pierce and fasten tissue with one or more fasteners and resect tissue.

FIGS. 6A and 6B show a side view of apparatus 601, similar to apparatus 101, including anvil 602, first body 608, second body 604, and proximal elongate member 644 of a cartridge (not shown) extending through second body 604. As shown in FIGS. 6A and 6B, proximal elongate member 644 may be back fed through working channel 610 of endoscope 603 when coupling apparatus 601 to endoscope 603. Distal front face 620 may contact a portion of apparatus 601 once first body 608 is coupled to the distal tip of endoscope 603.

Figure 7:
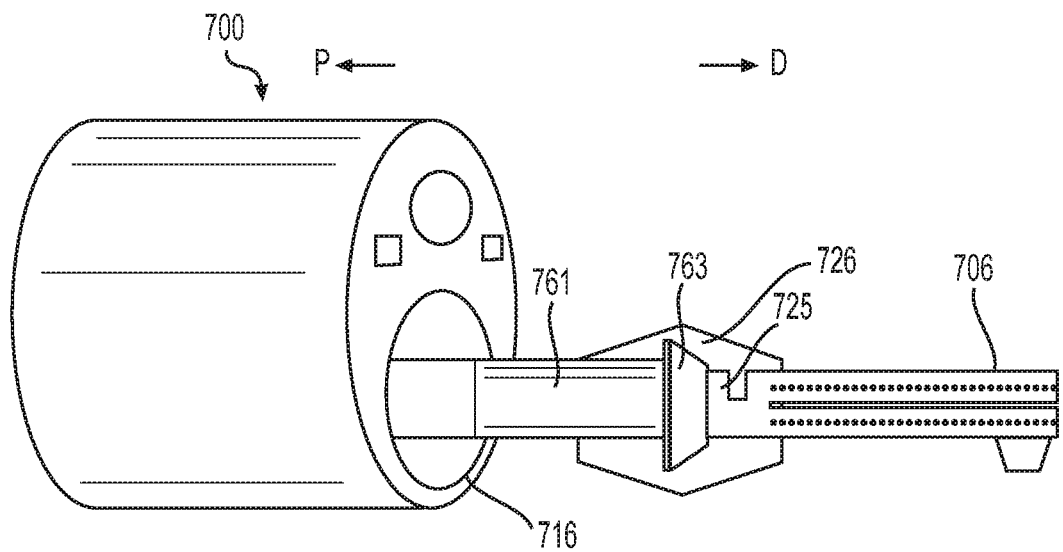
FIG. 7 is a side view of an exemplary medical device, according to aspects of this disclosure.

FIG. 7 shows an alternative embodiment of a cartridge 706 and proximal elongate member 761 extending out of working channel 716 of distal end 700 of a medical device. Cartridge 706 may include a coupling protrusion 725, having any one or more features of coupling protrusion 125. Surfaces of cartridge 706 may include cuts, slots, ridges, or other features that add flexibility to cartridge 706, permitting cartridge 706 to more easily extend through channel 716. Cartridge 706 may be coupled to proximal elongate member 761 via a coupler 763. Coupler 763 may mate with cartridge 706 and may be releasable via an actuator. In some examples, coupler 763 may contain an overmolded feature 726 in the shape of cartridge 706, and the overmolded feature 726 may be cylindrical. In some examples, an overmolded feature 726 of coupler 763 may be overmolded into the shape of cartridge 706 such that once cartridge 706 is closed onto tissue, the tension actuated on the entire assembly by the operator exceeds the material strength of coupler 763, and thus may propel elongate member 761 into the material of coupler 763, which may then release cartridge 706.

Figure 8:
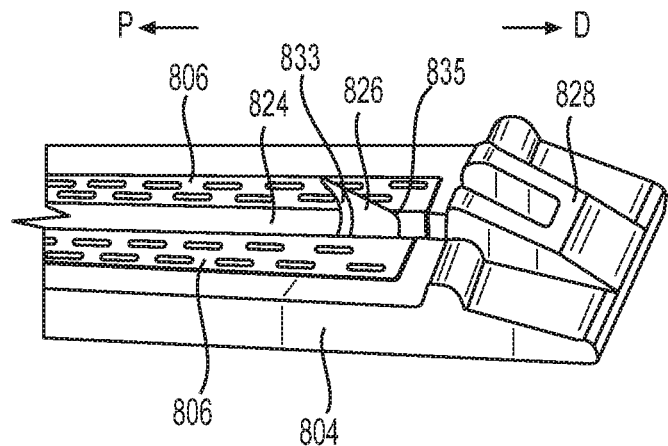
FIG. 8 is a perspective view of a portion of an exemplary medical device, according to aspects of this disclosure.

FIG. 8 shows a perspective view of a portion of second body 804, which is substantially similar to second body 104. Cartridge 806 is shown coupled to second body 804, and knife 826 has been moved from a cavity within distal portion 828 of second body 804 to within channel 824 of cartridge 806. Knife 826 may move through channel 824 to cut tissue of a patient prior to, during, or after deploying fasteners from cartridge 806 into tissue of the patient. Knife 826 includes a proximal-facing cutting edge 833 and a dull or otherwise atraumatic distal-facing edge 835, which may prevent unwanted cutting of tissue during operation as the device is moved distally.

Figure 9:
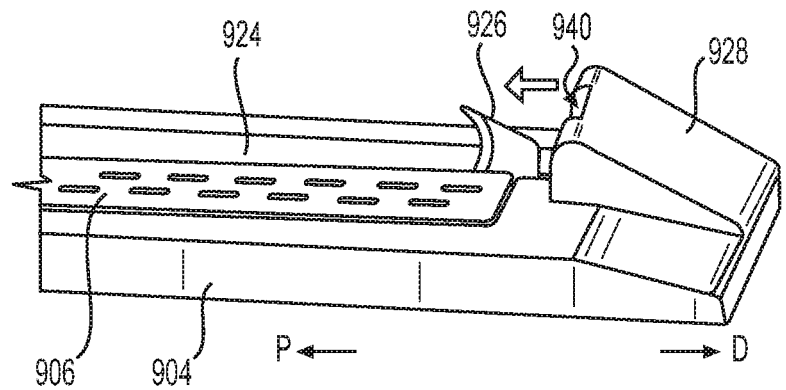
FIG. 9 is a perspective view of a portion of an exemplary medical device, according to aspects of this disclosure.

FIG. 9 shows a perspective view of an alternative embodiment of a second body 904 for use in an apparatus substantially similar to apparatus 101. In FIG. 9, cartridge 906 is positioned on only one side of channel 924 and extends parallel to channel 924. Channel 924 receives knife 926 from a cavity or pocket 940 within distal portion 928 of second body 904. By providing cartridge 906 on only one side of channel 924, a user may resect tissue of a patient and only fasten or staple a single side of the cut tissue. Either of second body 804 or second body 904 may be incorporated into and/or have any of the features previously described in relation to apparatus 101.

Figure 10A:
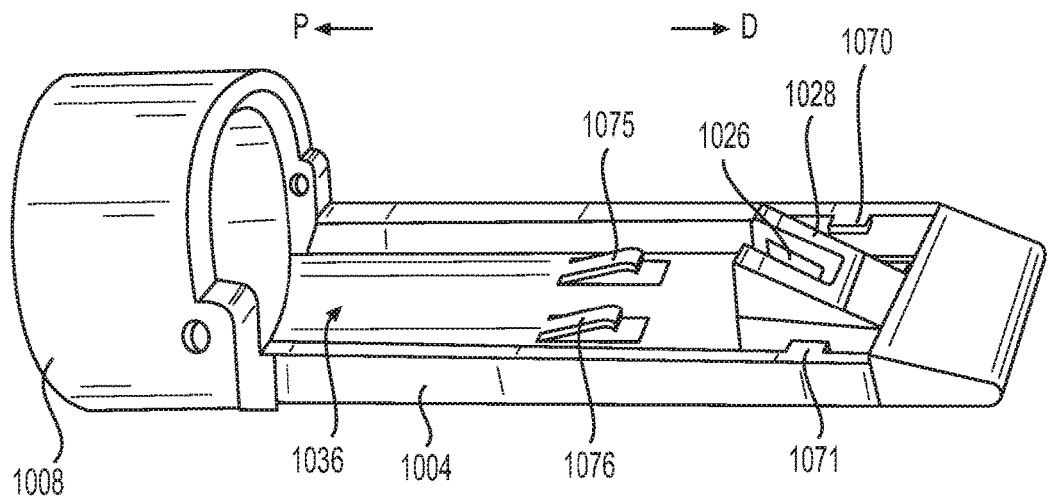
FIGS. 10A and 10B are perspective views of a portion of an exemplary medical device, according to aspects of this disclosure.
Figure 10B:
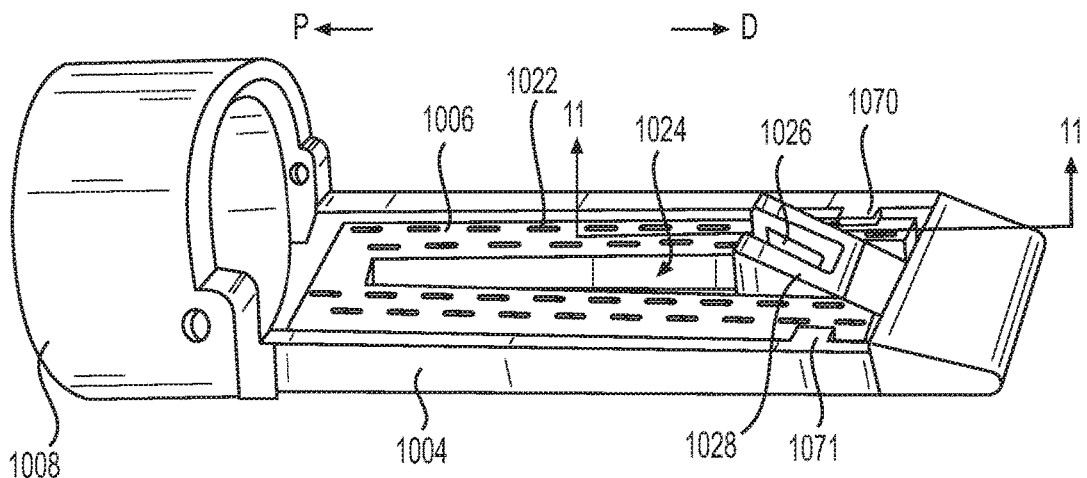
Figure 11:
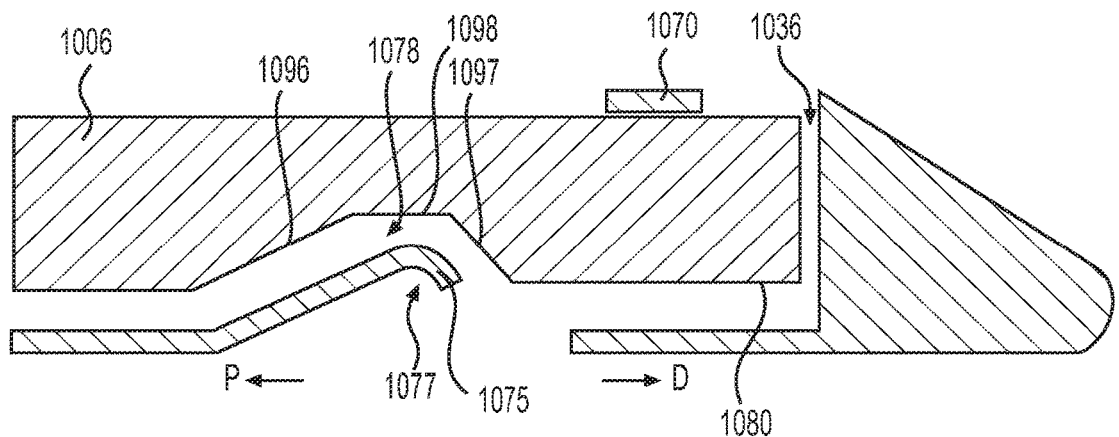
FIG. 11 is a side cross-sectional view of a portion of the exemplary medical device shown in FIG. 10B, according to aspects of this disclosure.

FIGS. 10A and 10B show perspective views of a portion an apparatus 1001 that may include any of the features previously described in relation to apparatus 101. Apparatus 1001 may include first body 1008, second body 1004, cartridge 1006 including slots 1022 for fasteners, and channel 1024 configured to receive knife 1026. Second body 1004 may include channel 1036 configured to receive cartridge 1006. A pair of flanges or tangs 1075, 1076 may extend from a surface defining channel 1036 and may be flexible. Tangs 1075, 1076 may be configured to bend such that a user may slide cartridge 1006 within channel 1036 and tangs 1075, 1076 will bend as a bottom surface 1080 of cartridge 1006 moves distally and contacts a surface defining channel 1036. When recesses 1078 in bottom surface 1080 align with tangs 1075, 1076, tangs 1075, 1076 may spring and/or move into recesses 1078. Tangs 1075, 1076 may include a curved distal portion 1077 (shown in FIG. 11). Curved distal portion 1077 may be configured to slide along surfaces of cartridge 1006 to facilitate positioning tangs 1075, 1076 within recesses 1078 of cartridge 1006. Curved distal portion 1077 may be curved downward away from channel 1036. In some examples, curved distal portion 1077 may facilitate movement of cartridge 1006 proximally by deflecting tangs 1075, 1076 downward away from channel 1036 when distal surface 1097 of recess 1078 contacts tangs 1075, 1076 as cartridge 1006 is moved proximally. Edge protrusions 1070, 1071 may extend into a distal portion of channel 1036, above an upper surface of an inserted cartridge 1006, to hold cartridge 1006 within channel 1036. For example, a user may slide cartridge 1006 within channel 1036 and bend tangs 1075, 1076 as the user moves cartridge 1006 distally and positions a distal portion of cartridge 1006 under edge protrusions 1070, 1071 (shown in FIG. 11 in a cross-section view along lines 11-11 of FIG. 10B). Recesses 1078 of cartridge 1006 may be positioned such that tangs 1075, 1076 are received by recesses 1078 when a distal portion of cartridge 1006 is positioned under edge protrusions 1070, 1071. The combination of tangs 1075, 1076 positioned within recesses 1078, and edge protrusions 1070, 1071 over cartridge 1006, may hold cartridge 1006 within channel 1036. Recess 1078 of bottom surface 1080 may include an angled proximal surface 1096 and an angled distal surface 1097, and the angled distal surface 1097 may be angled less than ninety degrees relative to the longitudinal axis of cartridge 1006. In some examples, angled distal surface 1097 may be positioned at an angle relative to the longitudinal axis of cartridge 1006 larger than the angle relative to the longitudinal axis of the proximal surface 1096. Distal surface 1097 may be angled at a higher degree relative to proximal surface 1096 so that a greater force is required to remove cartridge 1006 from channel 1036 of second body 1004 (e.g. by moving cartridge 1006 proximally) compared to the force required to insert cartridge 1006 into channel 1036 (e.g. to position tangs 1075, 1076 within recess 1078 by moving cartridge 1006 distally). An intermediate surface 1098 of recess 1078 may be positioned between proximal surface 1096 and distal surface 1097, and intermediate surface 1098 may be substantially parallel to the longitudinal axis of cartridge 1006.

As shown in FIG. 10B, some embodiments of devices may include a knife 1026 positioned proximal to the distal end of cartridge 1006, including proximal to some distalmost slots 1022 and associated fasteners. By positioning knife 1026 at a starting position proximal to the end of cartridge 1006 and proximal to the distalmost slots 1022 of cartridge 1006, a user may staple the entire length of the tissue that knife 1026 cuts when moved proximally. For example, a user may clasp tissue between second body 1004 and an anvil (similar to anvil 102) to staple tissue together, and then may actuate knife 1026 to move knife 1026 proximally and cut a portion of tissue adjacent to the portion of tissue that has been stapled, without cutting beyond the distal end of the stapled tissue. Also, a distal front surface 1028 of second body 1004 may be distal to knife 1026 and may prevent knife 1026 from contacting tissue when knife 1026 is positioned at a distal end of channel 1024. For example, distal front surface 1028 may extend radially-inward relative to the central longitudinal axis of second body 1008 and may, in some examples, be angled to align with an edge of knife 1026.

Each of the aforementioned apparatuses and devices may be used to visualize, couple, and/or cut tissue. In some examples, a user may load proximal elongate member 144 of cartridge 106 in a working channel of an endoscope by backfeeding the proximal elongate member 144 through a distal end of an endoscope working channel to position a portion of proximal elongate member 144 within the working channel. Once the proximal elongate member 144 is positioned within a working channel, a handle assembly or actuation assembly may be coupled to the proximal end of the proximal elongate member 144. In other examples, the user may move cartridge 106 and proximal elongate member 144 through working channel 116 from a proximal portion of endoscope 103, through working channel 116, and couple cartridge 106 to second body 104 by moving a proximal portion of proximal elongate member 144 to move cartridge 106 within channel 136 and coupling protrusion 125 within recess 142. The user may then introduce the endoscope 103 into the patient's body and move the endoscope 103 towards a target area. The user may locate a target area (such as a tumor or other diseased tissue) present in a body lumen of a subject using the endoscope by directly visualizing the target area using an image sensor. When the distal end of the endoscope is positioned at the target area, the user may actuate the apparatus 101 to move anvil 102 to an open position creating a space between the stapler's anvil 102 and second body 104. The user may then move tissue from the target area between or close to the active portion of apparatus 101, e.g. the space between the stapler device's anvil 102 and second body 104. The user may use a tissue acquisition device, such as a grasper positioned within working channel 116 of endoscope 103, to pull tissue to the active portion of apparatus 101. Once tissue is positioned within the stapler device's active portion, the user may move the stapler device's anvil 102 to a closed position and clamp down on the grasped tissue with the apparatus 101. The user may then actuate an actuator in order to pull on an actuation wire, thus moving an actuation sled of the apparatus proximally. By moving the actuation sled or mechanism proximally via an actuator, the user may deploy fasteners from cartridge 106 into the clamped tissue and against anvil 102. In some examples, the user may actuate a knife 126 in the apparatus 101 to cut portions of the target tissue either before or after fastening tissue together via fasteners.

A stapler instrument according to an exemplary embodiment includes a fastener cartridge that may be removed and replaced during a procedure through a working channel of a medical device. Using such an instrument can decrease procedure duration and limit irritation and/or injury to the patient due to repeated removal and re-insertion of a medical device into a patient's body, caused by the need to replace a fastener cartridge of the stapler. Endoscopic stapling may be especially useful in endoscopic, outpatient procedures. The scope of this disclosure is defined by the attached claims and not the ability to solve a specific problem.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A fastening system, comprising:
    a medical device comprising an image sensor and a working channel;
    a coupling body having (1) a portion removably coupled to a distal end of the medical device, (2) a cartridge holder, and (3) an anvil pivotably coupled to the cartridge holder, wherein the cartridge holder and the anvil extend distally from the portion and extend distally of a distalmost face of the medical device;
    a flexible member extending through the working channel of the medical device; and
    a fastener cartridge coupled to a distal end of the flexible member, including at least one fastener, and configured for releasable coupling to the cartridge holder, wherein uncoupling of the fastener cartridge from the cartridge holder uncouples the flexible member from the coupling body, wherein the fastener cartridge is sized so as to be passable through the working channel, and wherein the flexible member is fixedly coupled to a proximal end of the fastener cartridge such that flexible member and the fastener cartridge are jointly movable proximally through the working channel following the uncoupling of the fastener cartridge from the cartridge holder.

2. The system of claim 1, wherein the fastener cartridge includes a cartridge protrusion having a first recess and a second recess, wherein the cartridge holder includes a holder recess having a first protrusion and a second protrusion, and wherein the holder recess is configured to receive the cartridge protrusion such that the first protrusion of the holder recess is received within the first recess of the cartridge protrusion and the second protrusion of the holder recess is received within the second recess of the cartridge protrusion.

3. The system of claim 2, wherein the holder recess is a first holder recess and the cartridge protrusion is a first cartridge protrusion, and the fastener cartridge includes a second cartridge protrusion, and wherein the cartridge holder includes a second holder recess configured to receive the second cartridge protrusion.

4. The system of claim 1, further comprising a knife for cutting tissue.

5. The system of claim 4, wherein the knife is configured to move from a cavity within the cartridge holder through a channel of the fastener cartridge.

6. The system of claim 5, wherein a distalmost end of the fastener cartridge is distal to the cavity when the fastener cartridge is coupled to the cartridge holder.

7. The system of claim 4, wherein the knife is configured to move proximally from a cavity at a distal portion of the cartridge holder, wherein the knife is positioned adjacent to the fastener cartridge and within a channel of the cartridge holder as the knife moves proximally.

8. The system of claim 4, wherein the knife includes a first proximally-facing sharp edge.

9. The system of claim 4, wherein the anvil includes a channel configured to receive the knife.

10. The system of claim 1, wherein the cartridge holder includes:
    a channel for receiving the fastener cartridge; and
    at least one tang extending into the channel;
    wherein the fastener cartridge includes at least one recess configured to receive the at least one tang, and wherein the at least one tang is positioned within the at least one recess when the fastener cartridge is coupled to the cartridge holder.

11. The system of claim 1, wherein the anvil includes a distal portion and two spaced-apart proximal portions extending from a proximal end of the distal portion, wherein each of the two proximal portions is pivotably coupled to the coupling body.

12. The system of claim 1, wherein the flexible member is a first flexible member, and wherein the system further comprises:
    a second flexible member coupled to the coupling body and configured to extend to a proximal portion of the medical device, and
    an actuation wire extending through the second flexible member, wherein the actuation wire is configured to move the anvil towards and/or away from the cartridge holder.

13. The system of claim 1, wherein the flexible member includes at least one actuation wire configured to deploy the at least one fastener from the fastener cartridge.

14. The system of claim 1, wherein the distal end of the flexible member is directly coupled to the fastener cartridge.

15. A fastening system, comprising:
    a medical device comprising an image sensor and a working channel;
    a coupling body having (1) a portion removably coupled to a distal end of the medical device, (2) a cartridge holder, and (3) an anvil pivotably coupled to the cartridge holder, wherein the cartridge holder and the anvil extend distally from the portion and are configured to extend distally of a distalmost face of the medical device when the portion is coupled to the distal end of the medical device;
    a flexible member extending through the working channel of the medical device; and
    a fastener cartridge fixedly coupled to a distal end of the flexible member, including at least one fastener, and configured for releasable coupling to the cartridge holder, wherein, in a configuration in which the fastener cartridge is uncoupled from the cartridge holder, the flexible member and the fastener cartridge are jointly movable relative to the coupling body into a configuration in which (a) a distal end of the flexible member and (b) a distalmost end of the fastener cartridge are proximal of a proximalmost end of the coupling body, and wherein, due to a size of the fastener cartridge and due to the fastener cartridge being fixedly coupled to the distal end of the flexible member, the flexible member and the fastener cartridge are jointly movable proximally through the working channel following an uncoupling of the fastener cartridge from the cartridge holder.

16. The system of claim 15, wherein the flexible member is a first flexible member, wherein the first flexible member includes a first actuator configured to deploy the at least one fastener from the fastener cartridge, and wherein the system further comprises:
    a second flexible member coupled to the coupling body and configured to extend to a proximal portion of the medical device, wherein the second flexible member includes a second actuator configured to move the anvil toward the cartridge holder.

17. The system of claim 15, wherein the distal end of the flexible member is fixedly coupled to a proximal end of the fastener cartridge.

18. A fastening system, comprising:
    a medical device including an image sensor and a working channel;
    a coupling body having (1) a portion configured to couple to a distal end of the medical device, (2) a cartridge holder, and (3) an anvil pivotably coupled to the cartridge holder, wherein the cartridge holder and the anvil extend distally from the portion and are configured to extend distally of a distalmost face of the medical device upon coupling of the portion to the distal end of the medical device;
    a first flexible member configured to extend through the working channel of the medical device;
    a fastener cartridge fixedly coupled to a distal end of the first flexible member, including at least one fastener, and configured for releasable coupling to the cartridge holder, wherein the first flexible member includes a first actuator configured to deploy the at least one fastener from the fastener cartridge, wherein, as a result of a size of the fastener cartridge and the fastener cartridge being fixedly coupled to the distal end of the first flexible member, the first flexible member and the fastener cartridge are configured to be jointly movable proximally through the working channel following an uncoupling of the fastener cartridge from the cartridge holder; and
    a second flexible member coupled to the coupling body and configured to extend, externally of a shaft of the medical device, to a proximal portion of the medical device, wherein the second flexible member includes a second actuator configured to move the anvil toward the cartridge holder.

19. The system of claim 18, wherein the distal end of the first flexible member is fixedly coupled to a proximal end of the fastener cartridge.

20. The system of claim 19, wherein the distal end of the first flexible member is directly coupled to the proximal end of the fastener cartridge.

* * * * *